(12) United States Patent
Sung et al.

(10) Patent No.: US 10,226,569 B2
(45) Date of Patent: Mar. 12, 2019

(54) RIGID REINFORCING EXOSKELETAL SLEEVE FOR DELIVERY OF FLOWABLE BIOCOMPATIBLE MATERIALS

(71) Applicant: Ethicon, Inc., Somerville, NJ (US)

(72) Inventors: An-Min Jason Sung, Warren, NJ (US); Dennis D. Jamiolkowski, Long Valley, NJ (US); Guanghui Zhang, Belle Mead, NJ (US)

(73) Assignee: Ethicon, Inc., Somerville, NJ (US)

( * ) Notice: Subject to any disclaimer, the term of this patent is extended or adjusted under 35 U.S.C. 154(b) by 227 days.

(21) Appl. No.: 15/137,202

(22) Filed: Apr. 25, 2016

(65) Prior Publication Data

US 2016/0235909 A1 Aug. 18, 2016

Related U.S. Application Data

(62) Division of application No. 13/556,790, filed on Jul. 24, 2012, now abandoned.

(51) Int. Cl.

| *A61M 5/14* | (2006.01) |
|---|---|
| *A61B 17/34* | (2006.01) |
| *A61M 25/02* | (2006.01) |
| *A61B 17/00* | (2006.01) |
| *A61M 5/142* | (2006.01) |

(52) U.S. Cl.
CPC ..... *A61M 5/1414* (2013.01); *A61B 17/00491* (2013.01); *A61B 17/34* (2013.01); *A61B 17/3415* (2013.01); *A61M 5/1424* (2013.01); *A61M 25/02* (2013.01); *A61B 2017/00331* (2013.01); *A61B 2017/00469* (2013.01);

(Continued)

(58) Field of Classification Search
CPC .............. A61B 17/00491; A61B 17/34; A61B 17/3415; A61B 2017/00331; A61B 2017/00469; A61B 2017/3405; A61B 2017/347; A61M 2005/1416; A61M 25/02; A61M 5/1414; A61M 5/1424
See application file for complete search history.

(56) References Cited

U.S. PATENT DOCUMENTS

| 5,146,925 A | 9/1992 | Snow |
| 5,400,776 A | 3/1995 | Bartholomew |

(Continued)

FOREIGN PATENT DOCUMENTS

| EP | 2436418 A1 | 4/2012 |
| WO | WO 00/67830 A1 | 11/2000 |

(Continued)

*Primary Examiner* — Imani Hayman

(57) ABSTRACT

Exoskeletal devices or sleeves that can be used with the delivery tube of an applicator device to help dispense fluids, typically flowable biocompatible materials such as hemostatic agents, adhesives, or sealants, onto specific sites in the human body for a medical reason are disclosed. The exoskeletal devices or sleeves are rigid, pre-shaped, and snappably or slidably affixed to the delivery tube. The exoskeletal devices or sleeves do not come into contact with the flowable biocompatible fluid being dispensed, and they can be placed at any position along the delivery tube to address different application situations. Once the exoskeletal device or sleeve is in place, it can optionally be locked onto the delivery tube to prevent further sliding under stresses when pushed against tissue. Multiple exoskeletal devices or sleeves can also be used to achieve more complicated shapes for hard-to-reach anatomical sites.

3 Claims, 17 Drawing Sheets

(52) U.S. Cl.
CPC . *A61B 2017/3405* (2013.01); *A61B 2017/347* (2013.01); *A61M 2005/1416* (2013.01)

(56) References Cited

U.S. PATENT DOCUMENTS

| | | |
|---|---|---|
| 5,461,200 A | 10/1995 | Norcia |
| 5,562,619 A | 10/1996 | Mirarchi |
| 5,769,702 A | 6/1998 | Hanson |
| 5,797,392 A | 8/1998 | Keldmann |
| 5,810,885 A | 9/1998 | Zinger |
| 6,224,587 B1 | 5/2001 | Gibson |
| 6,228,051 B1 | 5/2001 | Trumbull |
| 6,440,120 B1 | 8/2002 | Maahs |
| 6,802,822 B1 | 10/2004 | Dodge |
| 6,976,979 B2 | 12/2005 | Lawrence |
| 7,073,511 B2 | 7/2006 | Schroeppel |
| 7,198,066 B2 | 4/2007 | Kagenow |
| 7,637,901 B2 | 12/2009 | Lawrence |
| 7,731,681 B2 | 6/2010 | Schaer et al. |
| 2005/0273020 A1 | 12/2005 | Whittaker et al. |
| 2006/0180151 A1 | 8/2006 | Rinaldi |
| 2009/0088728 A1 | 4/2009 | Dollar |
| 2009/0209916 A1 | 8/2009 | Peindl |
| 2010/0049137 A1 | 2/2010 | Fischer |
| 2010/0121278 A1 | 5/2010 | Fowler |
| 2011/0092918 A1 | 4/2011 | Jensen |
| 2014/0148789 A1 | 5/2014 | Le et al. |

FOREIGN PATENT DOCUMENTS

| | | |
|---|---|---|
| WO | WO 2002094334 A1 | 11/2002 |
| WO | WO 2011047753 A1 | 4/2011 |

FIG. 1
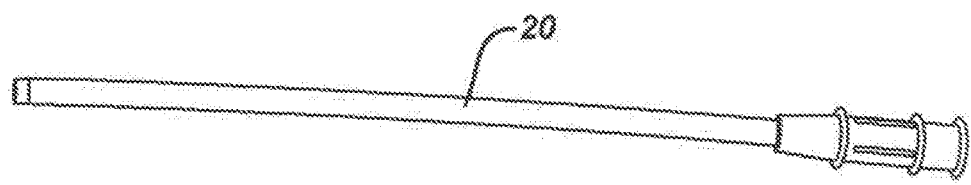
FIG. 2a   FIG. 2b   FIG. 2c
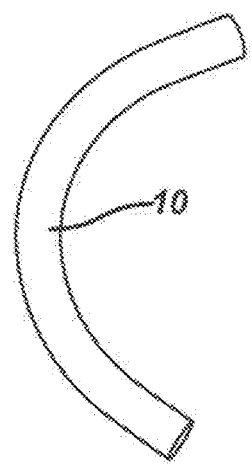 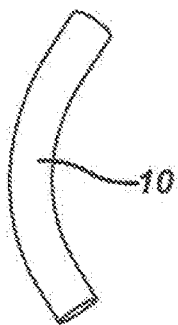 

RIGID REINFORCING EXOSKELETAL SLEEVE FOR DELIVERY OF FLOWABLE BIOCOMPATIBLE MATERIALS

CROSS-REFERENCE TO RELATED APPLICATIONS

This application is a divisional of U.S. patent application Ser. No. 13/556,790, filed Jul. 24, 2012, now abandoned. The complete disclosure of the aforementioned related patent application is hereby incorporated herein by reference for all purposes.

FIELD OF THE INVENTION

The invention relates to devices and methods for applying biocompatible fluids to a target anatomical site in the human body or in veterinary applications.

BACKGROUND OF THE INVENTION

This invention relates generally to devices and methods to help dispense fluids, typically flowable biocompatible materials such as hemostatic agents, adhesives, sealants, or adhesion prevention agents, onto specific sites in the human body for a medical reason. For example, during a laparoscopic procedure a surgeon makes at least one small incision in the patient's body near the area of interest. A cannula or trocar may be inserted into the incision for access. Various surgical instruments are introduced into the patient's body through the trocar(s) as needed. Particularly troublesome is the case of dispensing fluids such as hemostatic agents to a target anatomical site deep inside the body cavity, as the site may be accessible only through this narrow trocar. Many times, the pathway to the target anatomical site is narrow and torturous, not a straight line. Therefore, to reach the target anatomical site the dispensing or delivery tube needs to have an adequate length, be bent at the appropriate angle, and have sufficient rigidity to maintain this appropriate angle when pushed against tissue through the torturous space.

SURGIFLO® Hemostatic Matrix Kit by ETHICON, Inc., a Johnson & Johnson Company, is a medical or surgical kit containing an applicator device for hemostats and human thrombin. Specifically, the kit contains a pre-filled, flowable hemostat in a syringe and applicator tips. Before delivering the hemostatic agent, an applicator device tip, or delivery tube, is secured to the syringe via a Luer-lock connection. The flowable hemostat is applied to a target anatomical area by positioning the free end of the applicator tip near a target anatomical site and then expelling an amount of the flowable hemostat. The surgical or hemostatic applicator is supplied with two applicator tips for precise placement of the flowable. This gives surgeons an option of choosing between a flexible and malleable applicator tip that has "memory" to ensure it stays at the optimum angle for easier access and exact product placement, and a non-malleable tip that can be cut with nursing dressing scissors to a desired length for providing the required penetration depth. The flexible and malleable tube is shaped or formed, typically by manual bending, into a desired configuration.

While the non-malleable tip, which is a straight plastic tube, can be trimmed to a desired length for application, it is not conformable to hold an angle. The flexible and malleable tube, which contains an embedded malleable metal wire, can achieve and maintain angle(s) and can be used for tough to reach sites. The flexible and malleable dispensing or delivery tube, however, is tough to trim due to its embedded metal wire and has the potential to lose its shape when pushed against tissue, which can impact accurate delivery of the material at the desired location. If more rigid wire is used, it would be more difficult for the surgeon to trim the tube, and there would be the potential to damage the surrounding tissue when forcefully advancing the dispenser.

Accordingly, there is a need for a dispensing or delivery tube on an applicator device that is formable to a desired angle at the right distance and is easily cut to the desired length. Importantly, it should maintain its form when pushed against tissue in a narrow and torturous space and not damage the tissue. Its form should also be maintained especially when fluids with high viscosity are delivered through the delivery tube.

SUMMARY OF THE INVENTION

Exoskeletal sleeves for use with delivery or dispensing tubes of applicator devices used for applying an agent to a target anatomical site are disclosed. The sleeves are rigid, pre-shaped, slidable relative to the delivery tube, and hollow having an internal bore adapted to accept the delivery tube. In another embodiment, the sleeves comprise an elongated hollow member having an axial channel along the entire length. At least a portion of the channel has a width slightly smaller than an outside diameter of the delivery tube, and the sleeve is rigid, pre-shaped, and snappable onto the delivery tube. The sleeve of this alternative embodiment can also be slidable relative to the delivery tube. In either embodiment, the sleeves can have a pre-selected angle shape and/or a plurality of pre-selected angles. The sleeves can also further comprise a notch for receiving a lock.

Methods of delivering an agent to a target anatomical site using a delivery tube are also disclosed. These methods include positioning at least one exoskeletal sleeve described briefly above and herein on a delivery tube, maneuvering the applicator device to a target anatomical site, and expressing the agent through the delivery tube to the target anatomical site.

These and other objects of the invention will be apparent from the following description and appended claims and from practice of the invention.

BRIEF DESCRIPTION OF THE FIGURES

FIG. 1 illustrates an example of a delivery tube of an applicator device for use with the invention.

FIGS. 2a through 2c illustrate various embodiments of exoskeletal sleeves of the invention with different length, radii, and different angle of bend.

FIG. 7a illustrates an exoskeletal sleeve comprising a notch. FIG. 7b illustrates a horse-shoe or U-shaped lock. FIGS. 7c and 7d illustrate an exoskeletal sleeve comprising a horse-shoe or U-shaped lock wherein FIG. 7d is a side view of the sleeve.

FIG. 12a illustrates an exoskeletal sleeve comprising a notch. FIG. 12b illustrates a horse-shoe or U-shaped lock. FIGS. 12c and 12d illustrate an exoskeletal sleeve comprising a horse-shoe or U-shaped lock wherein FIG. 12d is a side view of the sleeve.

DETAILED DESCRIPTION OF THE INVENTION

Figure 3A:
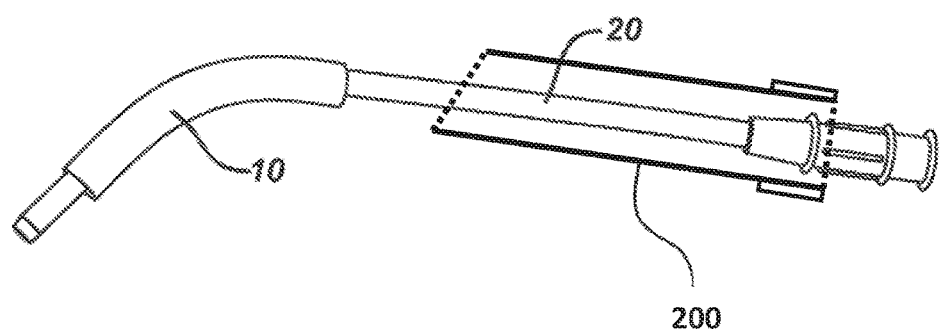
FIGS. 3a and 3b illustrate placement of an embodiment of an exoskeletal sleeve of the invention at different positions on the delivery tube of the applicator device shown in FIG. 1.

An objective of the invention is to help dispense fluids to a bodily target anatomical site during surgery through a very narrow and torturous space when the delivery tube is advanced forcefully against tissue. This invention addresses the limitation of maintaining the form of the delivery tube of other designs using either a bellows or accordion-like mechanism or a malleable wire. This invention further addresses the limitation of the malleable wire design of not being able to strike a good balance between being rigid or too soft. If it is too rigid, it would be difficult to trim to size. If it is too soft, then it does not hold the shape selected by the surgeon for the particular anatomical need.

The delivery or applicator device is a medical device and is broadly understood to include at least one reservoir for storing the component or agent to be delivered to an anatomical site such as a wound, tissue, or organ to be treated, and a delivery tube or conduit for expressing the agent to the site of action. The device may also include a component for mixing a plurality of agents.

This invention discloses the use of a rigid, pre-shaped exoskeletal sleeve or device over the delivery or dispensing tube. The exoskeletal sleeve or device does not come into contact with the flowable biocompatible fluid being dispensed and is positioned on the outside of the delivery conduit or delivery tube. The invention further requires that the device is snappably or slidably affixed to the delivery tube. "Snappable" is understood to mean that the exoskeletal sleeve device can be pushed onto the tube, with the tube going through an axial channel in the sleeve, and snapped into place on the tube. "Slidable" is understood to mean that the sleeve can be positioned onto the tube by inserting the tube into an internal bore of the sleeve and then sliding the sleeve along the tube into a desired position. If slidably affixed, the exoskeletal sleeve or device is preferably lockable. A further embodiment of the present invention is that device is snappably affixed, yet slidable until locked in place. That is, the device is initially snapped in place, but is free to slide along the tube to be positioned at the desired location, thus bending the tube at a desired angle at the right position; it is then locked in place so as to prevent undesirable movement.

The embodiments of the invention directed towards being snappably affixed, can refer to an embodiment of the rigid exoskeletal reinforcement with an elongated hollow member having an axial channel along the entire length to be used as a clip placed over the delivery tube. This embodiment can also include a locking mechanism to lock this exoskeletal device in place to prevent further sliding and losing its position. The invention also includes the use of multiple exoskeletal devices to allow the delivery tube to form complicated shapes to address hard-to-reach anatomical sites. A number of features used to secure the above embodiments onto the tubular dispenser are disclosed within.

The invention provides for exoskeletal devices or sleeves that can be used with the delivery tube of an applicator device such as the non-malleable applicator tip provided in the SURGIFLO® Hemostatic Matrix Kit. FIG. 1 illustrates an example of such an applicator tip or delivery tube or dispensing tube of an applicator device 20 for use with the invention. The exoskeletal device is used over the straight tube to bend the delivery tube to a desired angle and provide localized rigidity to hold the selected angle. The exoskeletal device does not become part of the delivery tube and does not come into contact with the agent. The exoskeletal device can be placed at any position along the delivery tube to address different application situations, and the delivery tube remains easy to trim or cut. Once the device is in place, it can optionally be locked onto the delivery tube to prevent further sliding under stresses when pushed against tissue. Multiple devices can also be used to achieve more complicated shapes for hard-to-reach anatomical sites.

The exoskeletal devices or sleeves of the invention described herein maintain their form under stress and provide localized rigid support that will not cause tissue damage. The exoskeletal devices or sleeves of the invention give surgeons the freedom to use multiple combinations of the devices to achieve complex shapes. The invention also provides means for locking the exoskeletal devices or sleeves onto the delivery tube, which secures the exoskeletal devices or sleeves against sliding once in place to help maintain its form in a tight space.

The exoskeletal devices or sleeves of the invention described herein use no metallic inserts and are easier to manufacture compared to that used for the flexible and malleable applicator tip provided in the SURGIFLO® Hemostatic Matrix Kit. In addition, cutting the delivery or dispensing tube to a desired length generates no sharp metallic endpoint associated with malleable systems with a metallic insert. Because there is no metallic insert, cutting the tube to desired length is easier to accomplish. The material used to make the exoskeletal devices or sleeves of the invention is also less expensive than the material used to make the flexible and malleable applicator tip provided in the SURGIFLO® Hemostatic Matrix Kit. Since the exoskeletal devices or sleeves of the invention are not part of the delivery tube, the overall cost of the manufacturing process for the exoskeletal devices or sleeves is reduced. The sleeves of the current invention can be manufactured by a number of known processes, including injection molding, extrusion, machining, and combinations thereof.

Figure 3B:
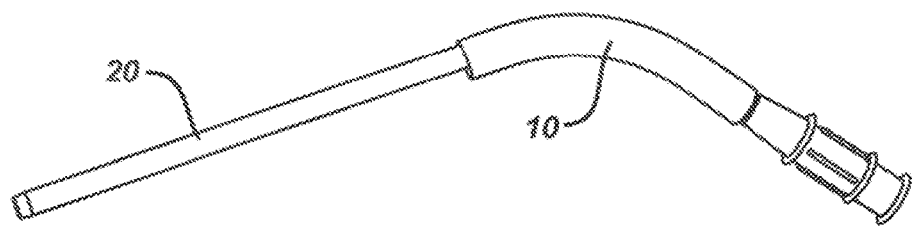

FIGS. 2a through 2c illustrate various embodiments of exoskeletal sleeves 10 of the invention with different length and radii. The exoskeletal sleeves 10 shown in FIGS. 2a through 2c are for use with a delivery tube 20 for applying an agent to a target anatomical site. The sleeves 10 are rigid, pre-shaped, slidable relative to the delivery tube 20 (not shown), and hollow having an internal bore adapted to accept the delivery tube 20. By slidable relative to the delivery tube 20, it is meant that the exoskeletal devices 10 can be slid onto the delivery tube 20 of an applicator device and placed at any position along the tube to address different application situations, as shown in FIGS. 3a and 3b. The exoskeletal sleeves are slidably affixed to the straight delivery tube 20 to bend the tube 20 at a desired angle and provide localized rigidity to hold said desired angle.

Figure 4A:
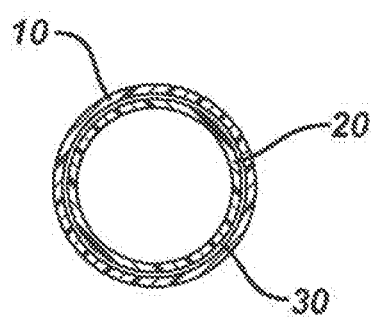
FIGS. 4a through 4g illustrate cross section views of exoskeletal sleeves of the invention with the delivery tube.
Figure 4B:
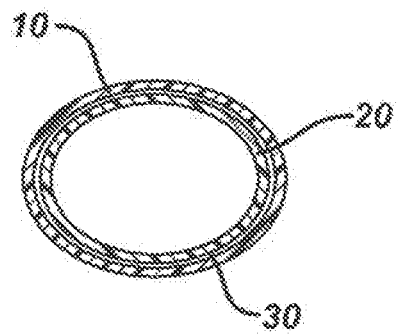
Figure 4C:
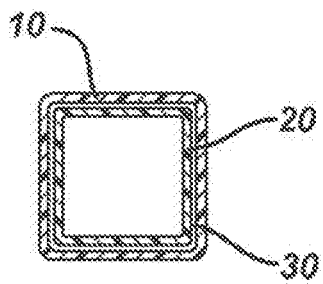
Figure 4D:
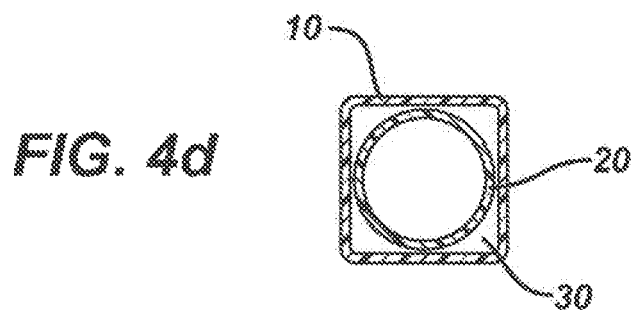
Figure 4E:
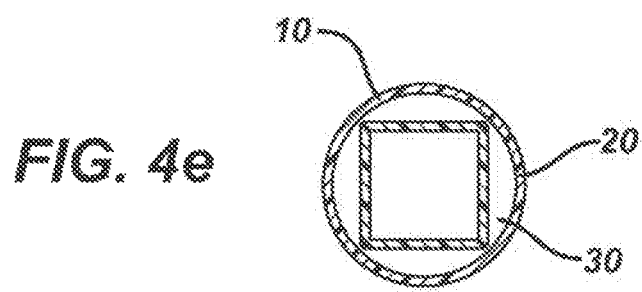
Figure 4F:
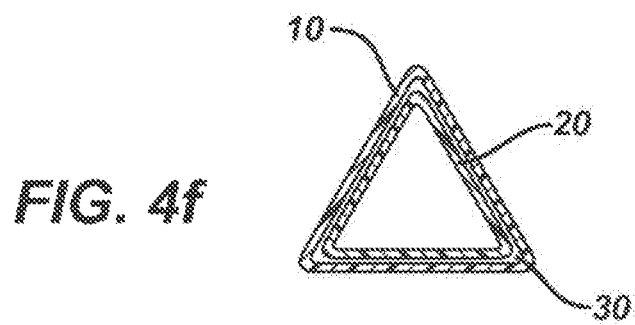
Figure 4G:
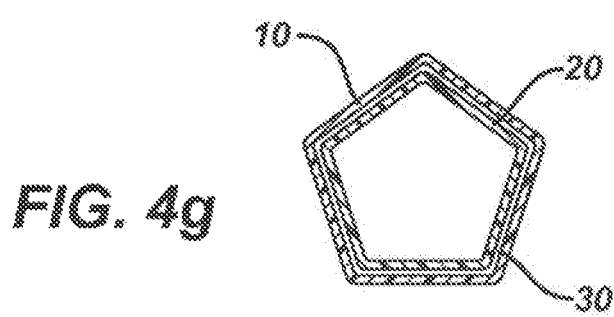
Figure 5A:
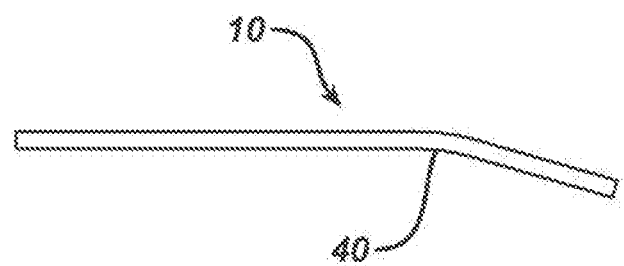
FIGS. 5a and 5b illustrate the pre-selected angle shape or bend in an exoskeletal sleeve of the invention.
Figure 5B:
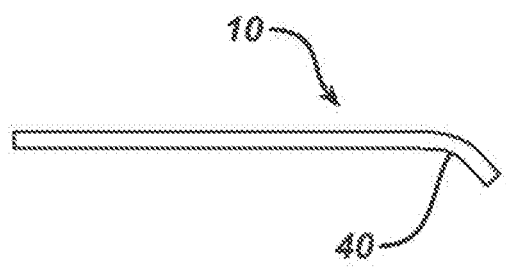
Figure 6A:
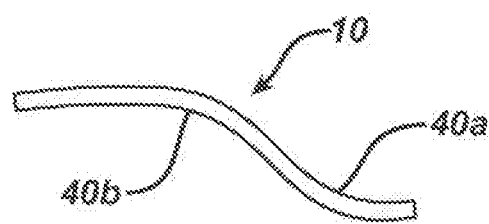
FIGS. 6a through 6d illustrate top views of exoskeletal sleeves of the invention having more than one pre-selected angle or bend that can be in one plane or in different planes.
Figure 6B:
Figure 6C:
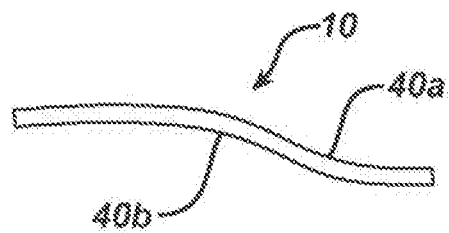
Figure 6D:
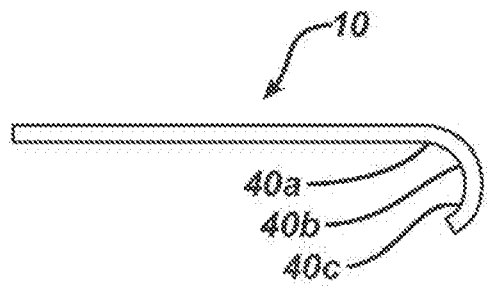
Figure 7A:
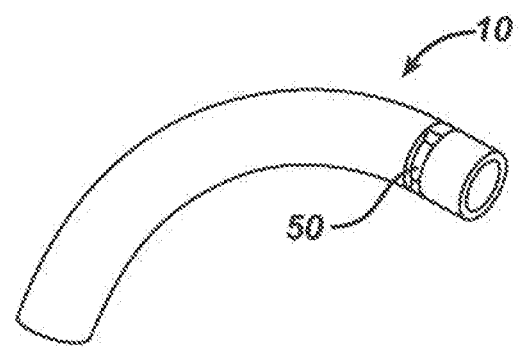
FIGS. 7a through 7d illustrate a means of locking an exoskeletal device onto a delivery tube.
Figure 7B:
Figure 7C:
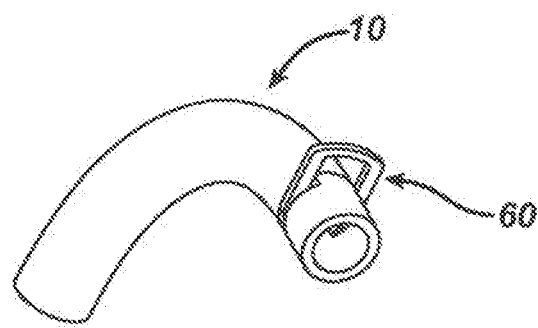
Figure 7D:
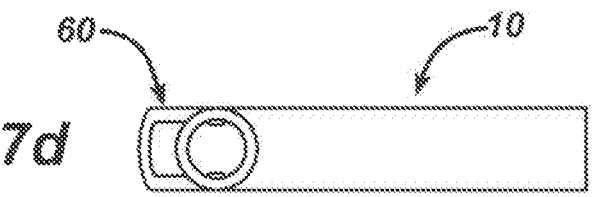

FIGS. 4a through 4g illustrate cross section views of exoskeletal sleeves 10 of the invention with the delivery tube 20. As can be seen in these figures, the internal bore 30 that accepts the delivery tube 20 can be any suitable shape, including circular (FIGS. 4a and 4e), elliptical (FIG. 4b), square (FIGS. 4c and 4d), triangular (FIG. 4f), or polygonal (FIG. 4g) shaped. The delivery tube 20 can have any suitable cross-section, such as, for example, circular (FIGS. 4a and 4d), elliptical (FIG. 4b), square (FIGS. 4c and 4e), triangular (FIG. 4f), or polygonal (FIG. 4g).

The exoskeletal sleeves 10 can have a pre-selected angle shape or bend 40 as shown in FIGS. 2a through 2c and FIGS. 5a and 5b. The sleeves 10 can also have a plurality of pre-selected angles 40. As illustrated in FIGS. 6a through 6d, the exoskeletal sleeves 10 of the invention can have two or more pre-selected angles or bends 40, 40a, 40b, 40c that can be in one plane or in different planes. The pre-selected angle shapes or bends can be any degree of angle and same or different from each other. The angle is generally from just under 180 degrees (180 degrees corresponding to straight sleeve), such as 170 or 150 degrees to about 90 degrees to about 0 degrees (corresponding to a U-shaped sleeve). Preferred angles are 160 degrees to 90 degrees, more preferably 150 to 130 degrees.

The range of bend radius which can be further defined as radius of curvature of the sleeve in the area of bend for a rigid, pre-shaped exoskeletal device 10 with a circular internal bore 30 is from about 0.5 inch to about 3 inches with a preferred range between 1 inch and 2.5 inches. The length of rigid pre-shape exoskeletal device ranges from about 0.5 inch to about 20 inches and preferably between 0.75 inch to 1.5 inches. The inside diameter (ID) of this slidable embodiment of the device is at least 0.001 inch, more preferably 0.005 inch larger than the outside diameter (OD) of the delivery tube. This clearance can be up to about 0.04 inch with the preferable clearance of approximately 0.01 inch to 0.03 inch. The thickness of the device (i.e. wall thickness) can vary; values between about 0.002 inch to 0.2 inch may be suitable, depending on the choice of material of fabrication. An important point is to have the right combination of material and wall thickness to maintain rigidity to hold the pre-selected angle. A successful material may be a thermoplastic or thermoset, but would need to have a modulus that would allow the device to hold the pre-selected angle at a given thickness of the sleeve. For example, a material such as polyvinylidene difluoride (PVDF) does hold the tube at a pre-selected angle with a wall thickness of 0.030 inch.

In one embodiment, the exoskeletal sleeve 10 has an internal diameter (ID) from about 0.01 inch to about 0.75 inch and a length covering from about 2 percent to about 100 percent of the delivery tube. In another embodiment, the exoskeletal sleeve 10 has a length covering from about 10 percent to about 75 percent of the delivery tube. In yet another embodiment, the exoskeletal sleeve 10 has a length from about 0.2 inch to about 20 inches long. In yet another embodiment, the exoskeletal sleeve 10 has a wall thickness from about 0.004 inch to about 0.2 inch.

To ensure that the exoskeletal device 10 stays in place once it is at the selected position, a means of locking the device onto the delivery tube 20 of an applicator device can be incorporated as shown in FIG. 7, which prevents sliding of the device 10 along the tube 20. One locking means, as illustrated in FIGS. 7a through 7d, are notches 50 (FIG. 7a) incorporated to receive a horse-shoe or U-shape lock 60 (FIG. 7b) to secure the exoskeletal device 10 onto the delivery tube 20 of an applicator device by providing a pinch force (FIGS. 7c and 7d). The delivery tube 20 of the applicator device can also have one or more preformed detents on its outer surface to act as receivers for the horse-shoe or U-shape lock 60.

Figure 8A:
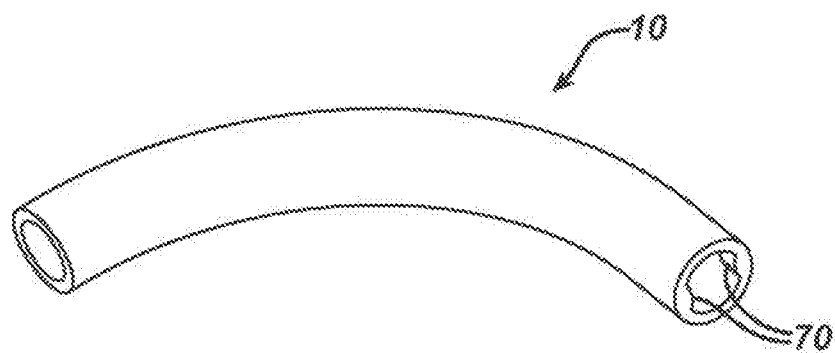
FIGS. 8a and 8b illustrate a means of locking an exoskeletal device onto a delivery tube incorporating a bump on an internal wall of the exoskeletal device.
Figure 8B:
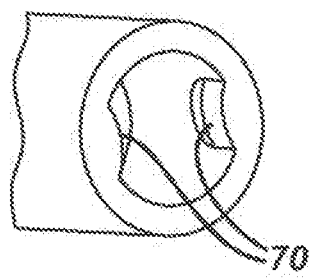

Another method to lock the exoskeletal sleeve 10 onto the applicator device delivery tube 20 is to incorporate one or more bumps 70 on an internal wall of the sleeve 10 as shown in FIGS. 8a and 8b. The bump 70 is adapted to provide additional friction between the sleeve 10 and the delivery tube 20. In one embodiment, the bump 70 has a height of from about 0.01 inch to about 0.12 inch. In another embodiment, the bump 70 has a height of 0.02 inch. In yet another embodiment, the bump 70 has a height of 0.03 inch. And in yet another embodiment, the bump 70 has a height of 0.04 inch. The bump or bumps 70 can be located anywhere along the internal wall of the exoskeletal sleeve 10, for example close to the ends or in the middle of the exoskeletal sleeve 10. The delivery tube 20 of the applicator device can also have one or more preformed detents on its outer surface to act as receivers for the bump 70. One or more bumps can be located at one or both ends of the exoskeletal sleeve 10, or anywhere on the exoskeletal sleeve 10, such as in the middle of the exoskeletal sleeve 10.

Figure 9A:
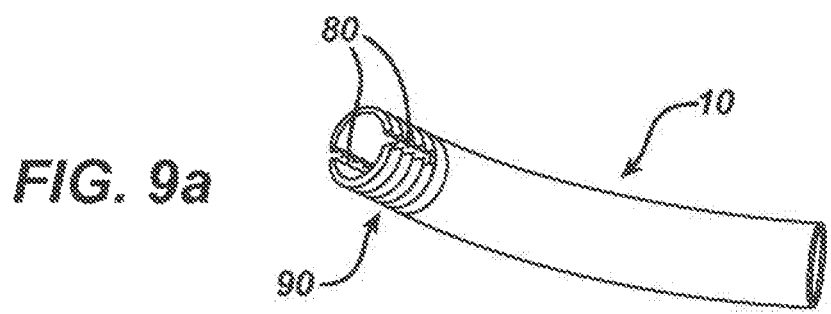
FIGS. 9a through 9c illustrate another means of locking an exoskeletal device onto a delivery tube incorporating a tightening nut threaded onto an end of the exoskeletal sleeve.
Figure 9B:
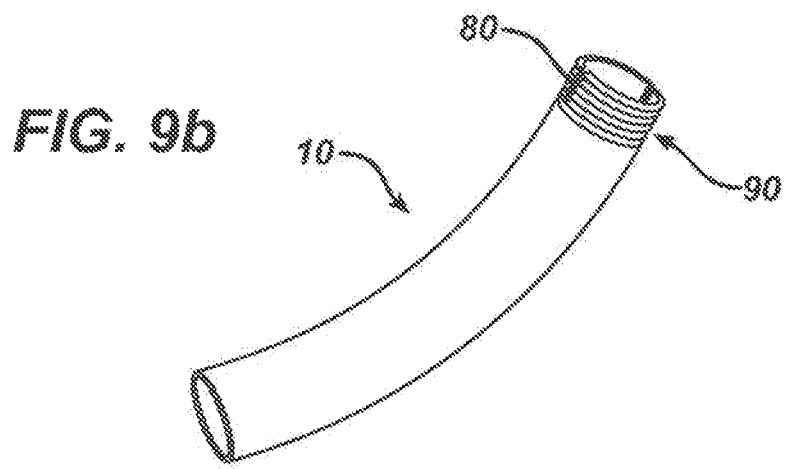
Figure 9C:
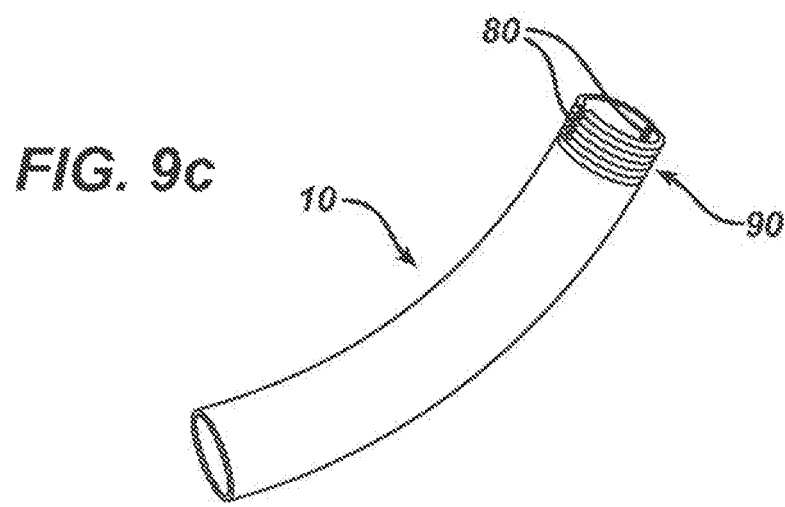

Another method to lock the exoskeletal sleeve 10 onto the applicator device delivery tube 20 incorporates a tightening nut threaded onto an end of the sleeve 10. The sleeve 10 has a thread on an external surface at said end, wherein said end has at least one slit. More specifically, another locking mechanism embodiment comprises a slotted end of the exoskeletal sleeve 10 in combination with a compression nut. In this embodiment, the sleeve 10 comprises at least one slit 80 at one end thereof as illustrated in FIGS. 9a through 9c. The slits 80 are fully penetrating the wall of the sleeve 10. At least one slit 80 is being present, more preferably two to six slits 80 or more slits 80, with two slits 80 shown in the embodiments illustrated in FIGS. 9a through 9c. The slit 80 width is about 0.5 to 5 times the wall thicknesses of the sleeve 10, or about 1 to 3 times the wall thicknesses, or about 0.02 to 0.08 inch. The slit 80 length is about 0.25 to about 2 times the external diameters of the sleeve 10, such as about 1 times the diameter of the sleeve 10. The threads 90 on the external surface of the sleeve 10 are threaded on the same end of the sleeve 10 where the slits 80 are present (slotted end of the sleeve). The threaded area covers at least the length of the slits 80, and can be up to 3 times longer versus the length of the slits 80, such as 2 times longer versus the length of the slits 80. In one embodiment, the slits 80 are 0.12 inch long, and the thread is 0.25 inch long.

Figure 10:
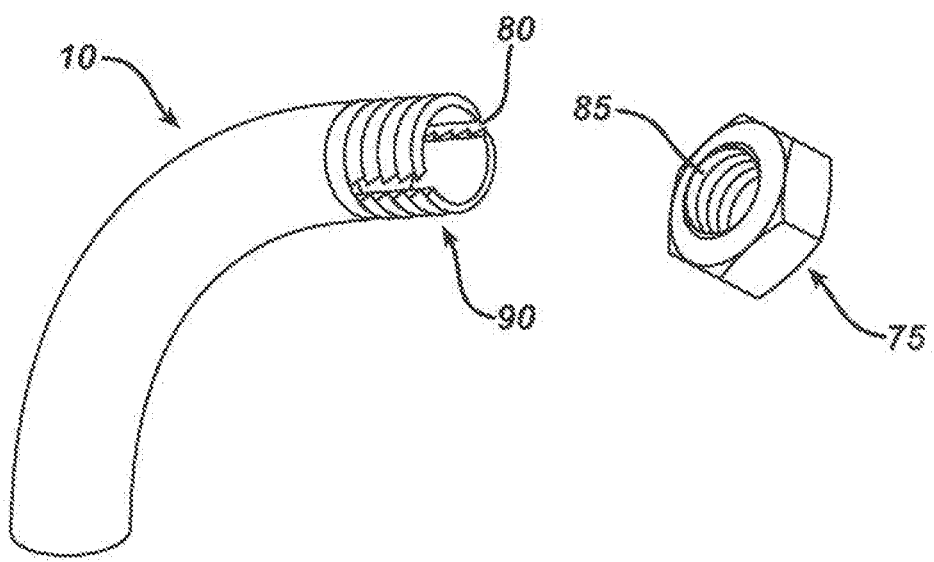
FIG. 10 further illustrates the means of locking an exoskeletal device onto a delivery tube incorporating a tightening nut threaded onto an end of the exoskeletal sleeve.

In use, a nut 75, shown in FIG. 10, having complementary thread 85 and adapted to compress the sleeve 10 upon threading onto the sleeve 10, is threaded onto the thread 90 on the sleeve 10; upon tightening of the nut 75, the sleeve 10 is compressed in the slotted 80 area against the inserted delivery tube 20 (not shown in FIG. 10), thus locking the position of the sleeve 10. Design of appropriate compression nuts is known in the art. In some designs, the nut has a conically shaped threaded opening, with wider opening at one end of the nut. In other designs, the internal diameter of the nut is smaller versus the external diameter of the sleeve 10, having 1 percent to 20 percent smaller diameter, such as 5 percent smaller diameter. It is also to be understood that the nut can be a wing nut, especially for use in open procedures.

In these and other designs of the compression nut 75 threaded on the compressible end of the sleeve 10, the threading of the nut 75 onto the sleeve 10 results in compression of the slotted 80 part of the sleeve 10 against the inserted delivery tube 20 thus immobilizing the sleeve 10 on the delivery tube 20 sufficiently to prevent undesired movement during positioning of the delivery tube 20 and during delivery of a fluid or agent to be ejected/delivered through the delivery tube 20.

Figure 11A:
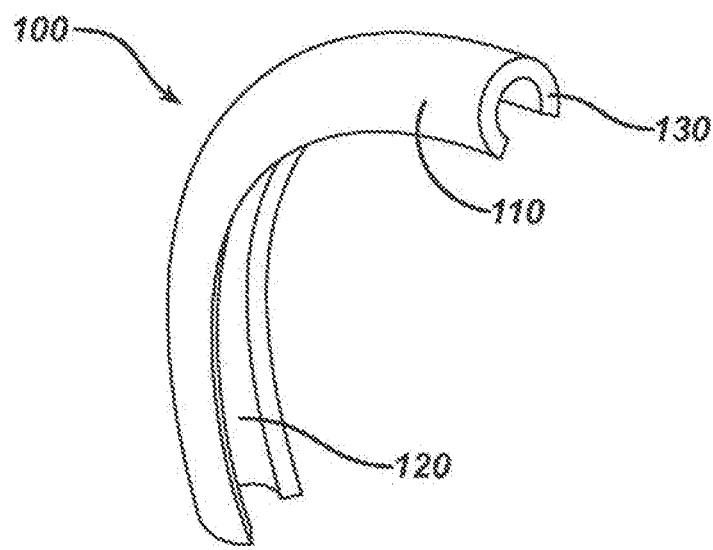
FIGS. 11a through 11d illustrate another embodiment of an exoskeletal sleeve of the invention that can be snapped onto the delivery tube.
Figure 11B:
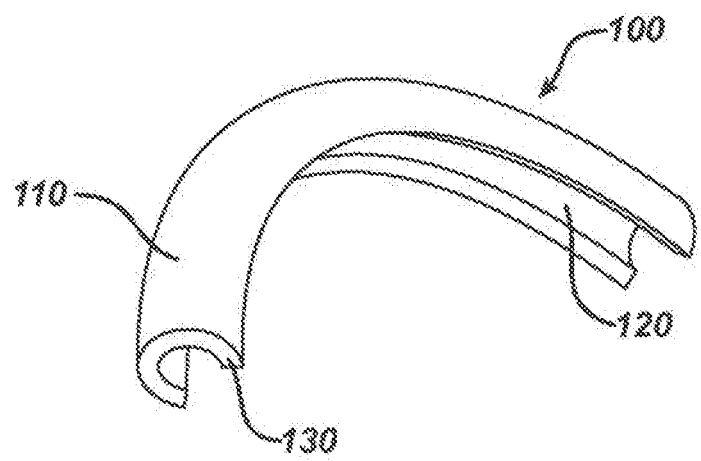

FIGS. 11a and 11b illustrate another embodiment of an exoskeletal sleeve 100 of the invention for use with delivery tube of an applicator device for applying an agent to a target anatomical site. In this embodiment, the exoskeletal sleeve 100 comprises an elongated member 110 having an axial channel 120 along the entire length of the member 110. The axial channel 120 is an opening formed by removing a portion of the sleeve wall along the main axis of the sleeve 100 as it is known in the mechanical arts by cutting or machining, or the axial channel 120 can be directly formed on the sleeve 100 as the sleeve 100 is extruded or molded. At least a portion of the channel 120 has a width slightly smaller than an outside diameter of the delivery tube (not shown in FIGS. 11a and 11b), which ensures that the sleeve stays in the selected position on the delivery tube. The exoskeletal sleeve 100 of this embodiment is rigid, pre-shaped, and snappable onto the delivery tube. By snappable, we mean that the exoskeletal sleeve 100 can act as a clip onto the delivery tube.

In another embodiment, the exoskeletal sleeve 100 is slidable relative to the delivery tube. By slidable relative to the delivery tube, it is meant that the exoskeletal devices 100 can be slid onto the delivery tube of an applicator device and placed at any position along the tube to address different application situations, similar to that as shown in FIG. 3 for exoskeletal device 10. The exoskeletal sleeves 100 are slidably affixed to a straight delivery tube to bend the tube at a desired angle and provide localized rigidity to hold said desired angle.

The exoskeletal sleeves 100 illustrated in FIGS. 11a and 11b can have a pre-selected angle shape or bend similar to embodiments shown in FIGS. 3 and 5. The sleeves 100 can also have a plurality of pre-selected angles as shown in the embodiments illustrated in FIG. 6. Similar to that illustrated in FIG. 6, the exoskeletal sleeves 100 of the invention can have two or more pre-selected angles or bends that can be in one plane or in different planes. The pre-selected angle shapes or bends can be any degree of angle as described above. The angle is generally from just under 180 degrees (180 degrees corresponding to straight sleeve), such as 170 or 150 degrees to about 90 degrees to about 0 degrees (corresponding to a U-shaped sleeve). Preferred angles are 160 degrees to 90 degrees, more preferably 150 to 130 degrees.

Optionally, the exoskeletal sleeve 100 can comprise a circular arc cross section 130, as shown in FIGS. 11a and 11b. The circular arc cross section 130 of the sleeve 100 can be an incomplete circle. In one embodiment, the circular arc cross section 130 of the sleeve 100 has an arc length of less than $2\pi R$, where R is the radius. In another embodiment, the circular arc cross section 130 of the sleeve 100 is over ½ to ⅞ of a full circle.

The length of rigid pre-shaped exoskeletal device ranges from about 0.5 inch to about 10 inches and preferably between 0.75 inch to 2 inches. The inside diameter (ID) of this snappable embodiment of the device can be smaller, equal, or larger than the outside diameter (OD) of the delivery tube. In certain embodiments, the inside diameter (ID) of this device is smaller by about 0.001 to about 0.01 inch versus the outside diameter (OD) of the delivery tube. In other embodiments, the inside diameter (ID) of this device is equal to the outside diameter (OD) of the delivery tube. In still other embodiments, the inside diameter (ID) of this device is at least 0.001 inch larger, more preferably 0.005 inch larger than the outside diameter (OD) of the delivery tube. This clearance can be up to about 0.04 inch with the preferable clearance of approximately 0.01 inch to 0.03 inch. With this tight tolerance, the exoskeletal sleeve 100 acts as a clip that is designed to stay in place once it is snappably affixed onto the delivery tube of the applicator device at the selected location. In other words, the width of this sleeve device 100 allows it to be snappably affixed to the delivery tube and slidable along the tube.

The thickness of the device (i.e. wall thickness) can vary; values between about 0.002 inch to 0.05 inch may be suitable, pending on the choice of material of fabrication. In yet another embodiment, the exoskeletal sleeve 100 has a wall thickness from about 0.004 inch to about 0.2 inch. An important point is to have the right combination of material and wall thickness to maintain rigidity to hold the pre-selected angle. A successful material may be a thermoplastic or thermoset, but would need to have a modulus that would allow the device to hold the pre-selected angle at a given thickness. For example, a material such as polyvinylidene difluoride (PVDF) does hold the tube at a pre-selected angle with a wall thickness of 0.030 inch, based on the prototypes made as described in Example 1.

In one embodiment, the exoskeletal sleeve 100 has a length covering from about 2 percent to about 100 percent of the delivery tube. In another embodiment, the exoskeletal sleeve 100 has a length covering from about 10 percent to about 75 percent of the delivery tube. In yet another embodiment, the exoskeletal sleeve 100 has a length from about 0.2 inch to about 20 inches long.

Figure 11C:
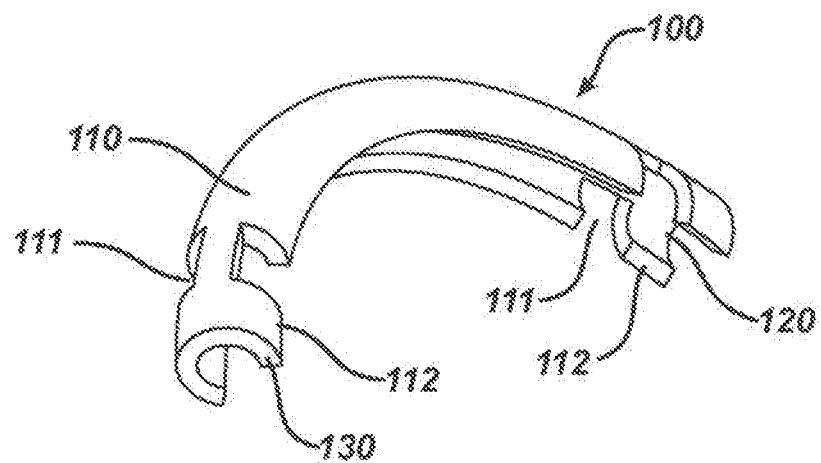

In an embodiment shown in FIG. 11c, the inventive sleeve 100 with an axial cutout or channel 120 has a variable width of the cutout 120, provided enough stiffness exists to maintain the desired bend angle. A plurality of areas of deeper cutouts 111 forms snappable features 112 which are narrower than the diameter of the delivery tube (not shown), which are separated by areas with deeper cutouts 111 which are wider than the diameter of the delivery tube. In another embodiment as shown in FIG. 11c, the snappable sections 112 are located at the proximal and distal ends of the sleeve 100 or in other words at the termini of the sleeve 100.

Figure 11D:
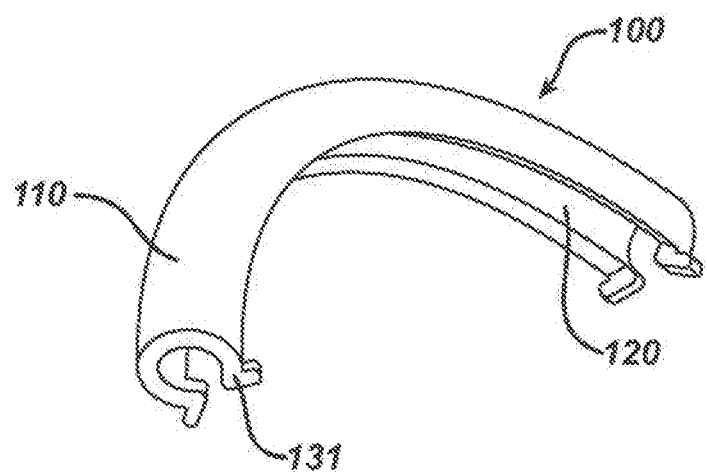

In an embodiment shown in FIG. 11d, the inventive sleeve 100 with an axial cutout 120 has a cross-section 131 substantially in a shape of a horseshoe, i.e. the edge of the cutout 120 is bent outwards so as to facilitate the snapping of the delivery tube (not shown) into the sleeve 100 through the cutout 120. It is further contemplated that the variable width of the cutout 120 in the sleeve 100 as shown in FIG. 11c can be used in combination with the horseshoe-like cross-sectional shape 131 of the sleeve 100 as shown in FIG. 11d.

Figure 12A:
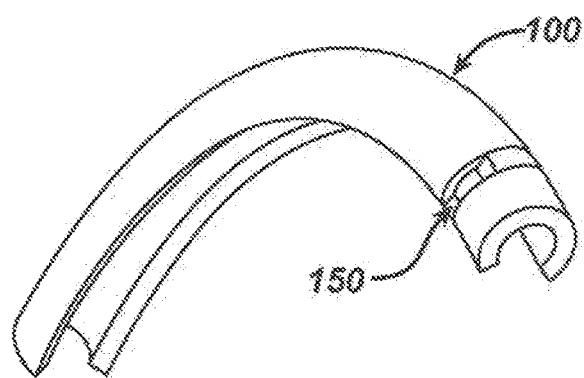
FIGS. 12a through 12d illustrate a means of locking an exoskeletal device illustrated in FIGS. 11a through and 11d onto a delivery tube.
Figure 12B:
Figure 12C:
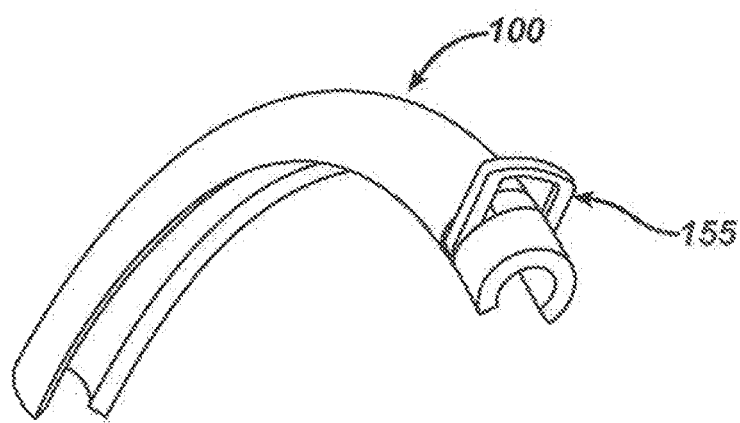
Figure 12D:
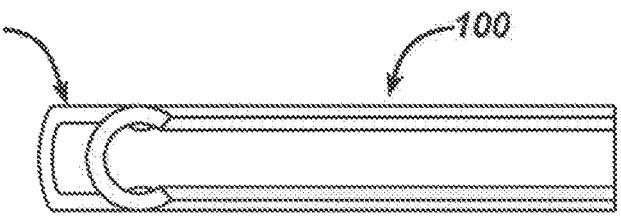

To ensure that the exoskeletal device 100 stays in place once it is at the selected position, a means of locking the device onto the delivery tube of an applicator device can be incorporated, similar to the locking mechanisms shown in FIGS. 7a through 7d, which prevents sliding of the device 100 along the tube. One locking means, as illustrated in FIGS. 12a through 12d, are notches 150 (FIG. 12a) incorporated to receive a horse-shoe or U-shape lock 155 (FIG. 7b) to secure the exoskeletal device 100 onto the delivery tube of an applicator device by providing a pinch force (FIGS. 12c and 12d). The delivery tube of the applicator device can also have one or more preformed detents on its outer surface to act as receivers for the horse-shoe or U-shape lock 155.

Figure 13A:
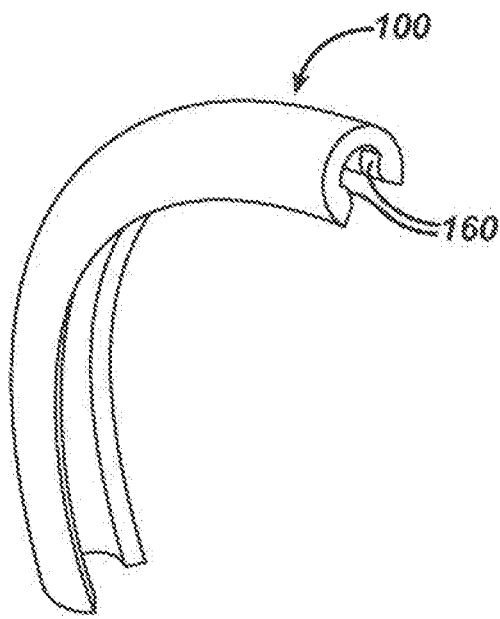
FIGS. 13a and 13b illustrate a means of locking an exoskeletal device illustrated in FIGS. 11a through 11d onto a delivery tube incorporating a bump on an internal wall of the exoskeletal device.
Figure 13B:
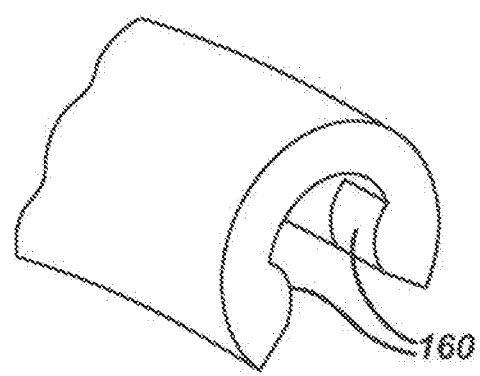

Another method to lock the exoskeletal sleeve 100 onto the applicator device delivery tube is to incorporate a bump on an internal wall of the sleeve, similar to the embodiments shown in FIGS. 13a and 13b. The bump 160 is adapted to provide additional friction between the sleeve 100 and the delivery tube. In one embodiment, the bump 160 has a height of from about 0.01 inch to about 0.12 inch. In another embodiment, the bump 160 has a height of 0.02 inch. In yet another embodiment, the bump 160 has a height of 0.03 inch. And in yet another embodiment, the bump 160 has a height of 0.04 inch. The bump or bumps 160 can be located anywhere along the internal wall of the exoskeletal sleeve 100, for example close to the ends or in the middle of the exoskeletal sleeve 10. The delivery tube of the applicator device can also have one or more preformed detents on its outer surface to act as receivers for the bump 160. One or more bumps can be located at one or both ends of the exoskeletal sleeve 100, or anywhere on the exoskeletal sleeve 100, such as in the middle of the exoskeletal sleeve 100.

In another embodiment, other-shaped protrusions or pinch points at one or more positions inside the exoskeletal sleeve 100 can be incorporated. These protrusions can be separate rubber-like balls/beads that get pushed in through a hole or notch similar to these shown in FIGS. 13a and 13b.

Figure 14:
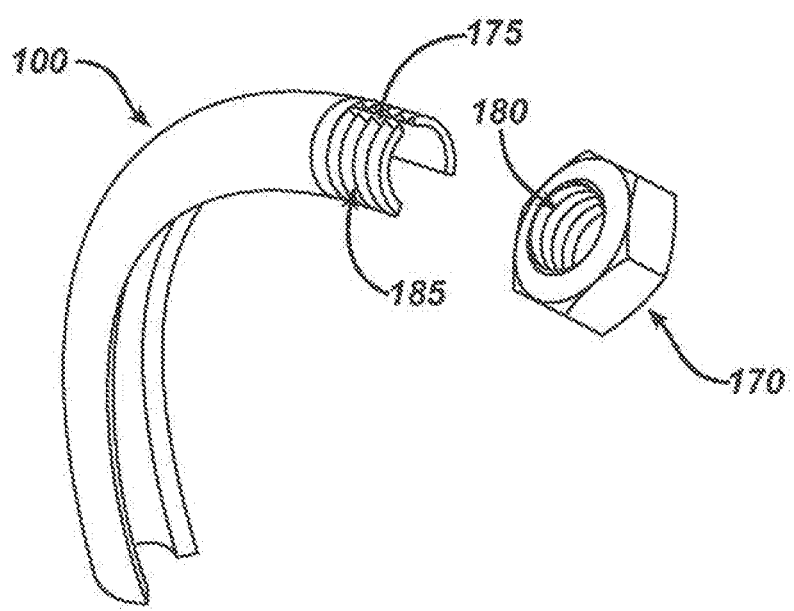
FIG. 14 further illustrates the means of locking an exoskeletal device illustrated in FIGS. 11a through 11d onto a delivery tube incorporating a tightening nut threaded onto an end of the exoskeletal sleeve.

Another method to lock the exoskeletal sleeve 100 onto the applicator device delivery tube incorporates a tightening nut 170 threaded onto an end of the sleeve 100, as shown in FIG. 14. The sleeve 100 has a thread 185 on an external surface at said end, wherein said end has at least one slit 175. More specifically, another locking mechanism embodiment comprises a slotted end of the exoskeletal sleeve 100 in combination with a compression nut 170. In this embodiment, the sleeve 100 comprises at least one slit 175 at one end thereof as illustrated in FIG. 14. The slit or slits 175 are fully penetrating the wall of the sleeve 100. At least one slit 175 is being present. The slit 175 width is about 0.5 to 5 times the wall thicknesses of the sleeve 100, or about 1 to 3 times the wall thicknesses, or about 0.02 to 0.08 inch. The slit 175 length is about 0.25 to about 2 times external diameters of the sleeve 100, such as about 1 times the diameter of the sleeve 100. The threads 185 on the external surface of the sleeve 100 are threaded on the same end of the sleeve 100 where the slit or slits 175 are present (slotted end of the sleeve). The threaded area 185 covers at least the length of the slit or slits 175, and can be up to 3 times longer versus the length of the slit or slits 175, such as 2 times longer versus the length of the slit or slits 175. In one embodiment, the slit or slits 175 are 0.12 inch long, and the thread 185 is 0.25 inch long.

In use, a nut 170, shown in FIG. 14, having complementary thread 180 and adapted to compress the sleeve 100 upon threading onto the sleeve 100, is threaded onto the thread 185 on the sleeve 100; upon tightening of the nut 170, the sleeve 100 is compressed in the slotted 175 area against the inserted delivery tube (not shown in FIG. 14), thus locking the position of the sleeve 100. Design of appropriate compression nuts is known in the art. In some designs, the nut has a conically shaped threaded opening, with wider opening at one end of the nut. In other designs, the internal diameter of the nut is smaller versus the external diameter of the sleeve 100, having 1 percent to 20 percent smaller diameter, such as 5 percent smaller diameter. It is also to be understood that the nut can be a wing nut, especially for use in open procedures.

In these and other designs of the compression nut 170 threaded on the compressible end of the sleeve 100, the threading of the nut 180 onto the sleeve 100 results in compression of the slotted 175 part of the sleeve 100 against the inserted delivery tube thus immobilizing the sleeve 100 on the delivery tube sufficiently to prevent undesired movement during positioning of the delivery tube and during delivery of a fluid or agent to be ejected/delivered through the delivery tube.

In one embodiment (not shown), the axial channel 120 of exoskeletal sleeve 100 has a different cutout arc at the proximate end and at the distal end, i.e. the arc of the axial channel 120 is variable from one end of the inventive sleeve to another. In another embodiment, the axial channel 120 of exoskeletal sleeve 100 has a cutout with radial cuts as shown in the cross-sectional view illustrated in FIG. 15a. In yet another embodiment the axial channel 120 of exoskeletal sleeve 100 has a cutout with non-radial cuts as shown in the cross-sectional view illustrated in FIG. 15b.

Figure 15A:
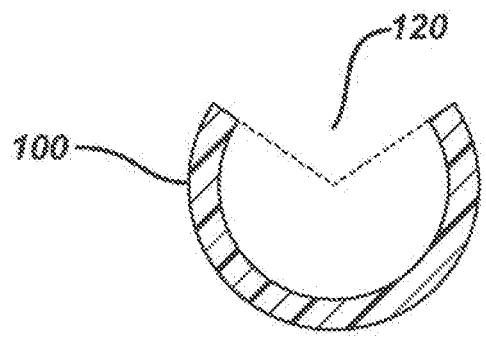
FIGS. 15a and 15b illustrate cross-sectional views of the exoskeletal sleeve illustrated in FIGS. 11a through 11d with an axial channel that has a cutout with radial cuts as shown in FIG. 15a or a non-radial cutout, as shown in FIG. 15b.

For the radial cutout of FIG. 15a, the cuts forming the axial channel 120 are drawn from the central axis of the sleeve 100, as shown schematically by the dashed lines. The external arc of the radial cutout shown in FIG. 15a (as defined on the OD of the sleeve) is the same as the internal arc of the radial cutout (as defined on the ID of the sleeve).

Figure 15B:
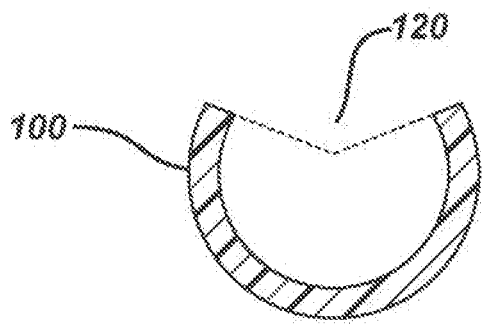

For the non-radial cutout of FIG. 15b, the cuts forming the axial channel 120 are not drawn from the central axis of the sleeve 100, as shown schematically by the dashed lines, but drawn from an axis which is closer to the axial channel 120. The external arc of the non-radial cutout shown in FIG. 15b (as defined on the OD of the sleeve) is larger than the internal arc of the non-radial cutout (as defined on the ID of the sleeve) by from 1 percent to about 20 percent.

A suitable material for the exoskeletal sleeves 10 and 100 described herein may be a thermoplastic or thermoset, but would need to have a modulus that would allow the device to hold the pre-selected angle at a given wall thickness at the temperatures normally encountered in the operating room, i.e. from 10 degrees Celsius to 50 degrees Celsius. Tensile modulus or Young's Modulus is the ratio of stress to strain within the elastic region of the stress-strain curve before the yield point. The preferred modulus is from about 100,000 to about 450,000 psi. For instance, acceptable materials include polyethylene with modulus of 120,000 psi, polyvinylidene fluoride (PVDF) with the modulus of 220,000 psi, and polyvinyl chloride (PVC) with the modulus of 410,000 psi.

The invention also provides a method of delivering an agent to a target anatomical site using a delivery tube. The method comprises the steps of positioning at least one exoskeletal sleeve 10 or 100, such as those disclosed and described above, on a delivery tube, maneuvering the delivery tube to the target anatomical site, and expressing the agent through the delivery tube to the target anatomical site. The method can optionally comprise the additional step of locking the exoskeletal sleeve 10 or 100 on the delivery tube before maneuvering the delivery tube to the target anatomical site.

The method can also comprise the step of positioning a plurality of exoskeletal sleeves 10 or 100 on said delivery tube before maneuvering the delivery tube to the target anatomical site. This can include using one or more embodiments of exoskeletal sleeves 10 and/or 100 such as those described herein. In one method, at least one of the exoskeletal sleeves can be positioned on the delivery tube at a distal end of the delivery tube from which the agent is delivered to a target anatomical site. In an alternative method, at least one of said exoskeletal sleeves can be positioned on the delivery tube on a middle section of the delivery tube. In yet another method, at least one of the exoskeletal sleeves can be positioned on a proximate end of the delivery tube from which the agent is delivered to a target anatomical site.

The above-described method of delivering an agent to a target anatomical site using a delivery tube can also comprise the step of maneuvering the delivery tube comprising at least one exoskeletal sleeve to the target anatomical site through a trocar 200 (shown in FIG. 3(*a*)). The exoskeletal sleeve can also be repositioned on the delivery tube during delivery of the agent without removing the delivery tube from the trocar 200.

EXAMPLE 1

Figure 16A:
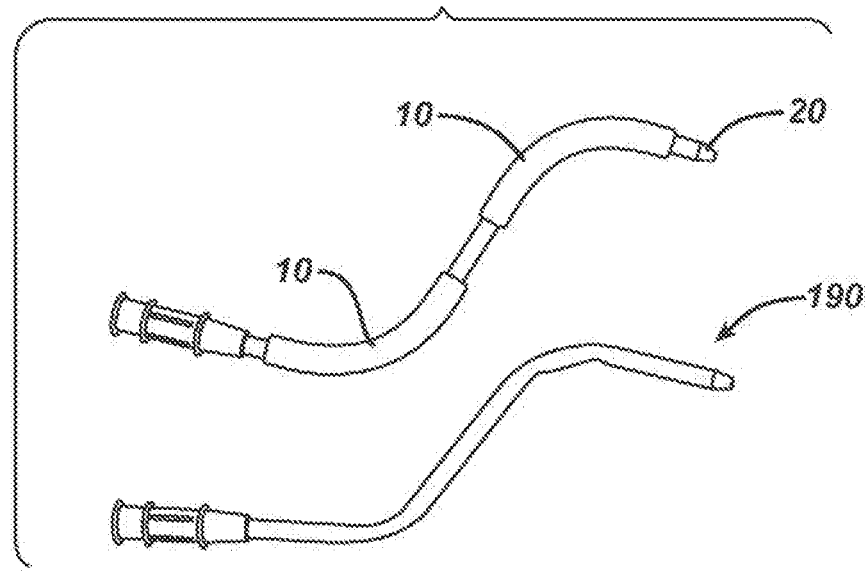
FIGS. 16a and 16b illustrate how the combination of a delivery tube of an applicator device and an exoskeletal sleeve can provide similar configuration of a flexible and malleable delivery tip or tube provided with a SURGIFLO® Hemostatic Matrix Kit.
Figure 16B:
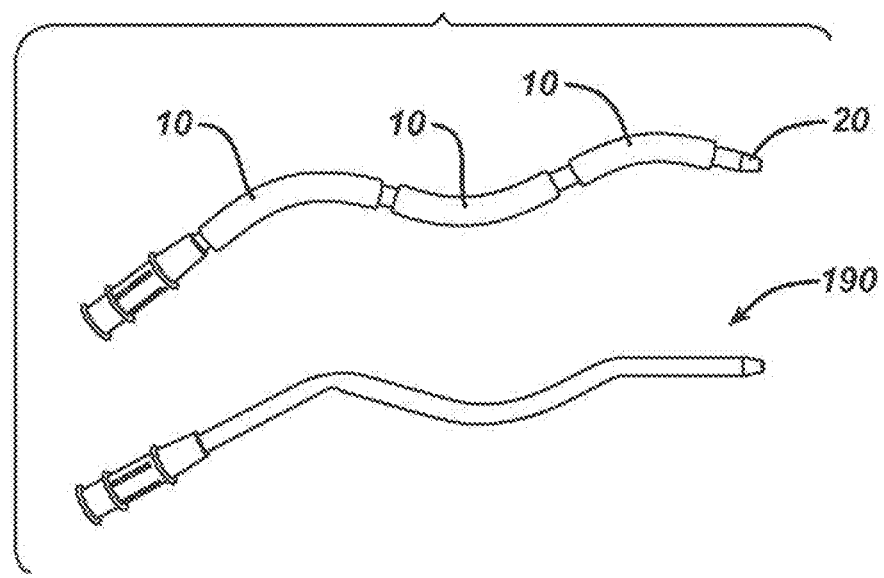

Three prototypes of the inventive slidable exoskeletal sleeves shown in FIGS. 2 and 3 were made of PVDF by cutting PVDF extruded tubing to size and then shaping it on a mandrel at elevated temperature of approximately 115 degrees Celsius. The bend radii of prototypes were, respectively, 2 inches, 2.5 inches, and 3 inches, and the internal diameter of the sleeves was 0.135 inch and the wall thickness was 0.030 inch. The sleeves manufactured by this method were slidably installed on a non-malleable delivery tip or delivery tube provided with a SURGIFLO® Hemostatic Matrix Kit. Moving the sleeves 10 along the delivery tube 20 and installing different sleeves 10 or several sleeves 10 at a time enabled various positions and angles selected, as illustrated in FIGS. 3 and 16. FIGS. 16*a* and 16*b* further illustrate how a flexible and malleable delivery tip or delivery tube 190 provided with a SURGIFLO® Hemostatic Matrix Kit can be shaped or formed by manual bending into a configuration similar to that formed using the inventive sleeves 10.

The invention being thus described, it will be apparent that the same may be varied in many ways. Such variations are not to be regarded as a departure from the spirit and scope of the invention, and all such modifications as would be obvious to one skilled in the art are intended to be included within the scope of the following claims.

We claim:

1. A method of delivering an agent to a target anatomical site using a delivery tube, said method comprising the steps of:
    positioning at least one exoskeletal sleeve on said delivery tube, wherein said at least one exoskeletal sleeve comprises an elongated member having an axial channel along an entire length, wherein at least a portion of said channel has a width slightly smaller than an outside diameter of the delivery tube, and wherein said sleeve is rigid, pre-shaped, and snappable onto the delivery tube, maneuvering said delivery tube to said target anatomical site through a trocar, and expressing said agent through said delivery tube to said target anatomical site.

2. The method of claim 1 further comprising the step of locking said at least one exoskeletal sleeve on said delivery tube before maneuvering said delivery tube to said target anatomical site through said trocar.

3. The method of claim 1 further comprising the step of repositioning the at least one exoskeletal sleeve on said delivery tube during delivery of the agent without removing said delivery tube from said trocar.

* * * * *